United States Patent
Cavallaro et al.

(10) Patent No.: US 6,793,625 B2
(45) Date of Patent: Sep. 21, 2004

(54) METHOD AND APPARATUS FOR CONCURRENTLY DISPLAYING RESPECTIVE IMAGES REPRESENTING REAL-TIME DATA AND NON REAL-TIME DATA

(75) Inventors: Samuel Cavallaro, Warner, NH (US); Dieter T. Ortlam, Beverly, MA (US)

(73) Assignee: Draeger Medical Systems, Inc., Danvers, MA (US)

( * ) Notice: Subject to any disclaimer, the term of this patent is extended or adjusted under 35 U.S.C. 154(b) by 144 days.

(21) Appl. No.: 09/992,887

(22) Filed: Nov. 6, 2001

(65) Prior Publication Data

US 2002/0147389 A1 Oct. 10, 2002

Related U.S. Application Data

(60) Provisional application No. 60/248,101, filed on Nov. 13, 2000.

(51) Int. Cl.$^7$ ................................. A61B 5/04
(52) U.S. Cl. ................... 600/440; 600/523; 600/525
(58) Field of Search .................. 600/437, 440, 600/509, 522–523, 525

(56) References Cited

U.S. PATENT DOCUMENTS

| | | | |
|---|---|---|---|
| 4,845,653 A | 7/1989 | Conrad et al. | 364/521 |
| 5,056,059 A | 10/1991 | Tivig et al. | 364/900 |
| 5,081,592 A | 1/1992 | Jenq | 364/487 |
| 5,140,519 A | 8/1992 | Friesdorf et al. | 364/413.03 |
| 5,210,872 A | 5/1993 | Ferguson et al. | 395/650 |
| 5,345,552 A | 9/1994 | Brown | 395/157 |
| 5,687,717 A | 11/1997 | Halpern et al. | 128/630 |
| 5,724,985 A * | 3/1998 | Snell et al. | 607/30 |
| 5,833,623 A * | 11/1998 | Mann et al. | 600/523 |
| 5,926,175 A | 7/1999 | Sturgeon et al. | 345/327 |
| 5,956,013 A | 9/1999 | Raj et al. | 345/134 |
| 5,987,345 A | 11/1999 | Engelmann et al. | 600/407 |
| 6,064,673 A | 5/2000 | Anderson et al. | 370/389 |
| 6,088,029 A | 7/2000 | Guiberson et al. | 345/247 |
| 6,104,948 A | 8/2000 | Bogart et al. | 600/524 |
| 6,174,283 B1 | 1/2001 | Nevo et al. | 600/301 |
| 6,511,426 B1 * | 1/2003 | Hossack et al. | 600/437 |

FOREIGN PATENT DOCUMENTS

| | | | |
|---|---|---|---|
| EP | 0 668 047 A2 | 8/1995 | A61B/5/00 |
| WO | WO 94/24631 * | 10/1994 | G06F/15/42 |
| WO | WO 98/13751 | 4/1998 | G06F/3/033 |
| WO | WO 00/46781 | 8/2000 | G09G/1/16 |

* cited by examiner

Primary Examiner—Carl H. Layno
(74) Attorney, Agent, or Firm—Jack Schwartz & Associates

(57) ABSTRACT

A method and apparatus for concurrently displaying respective images representing real-time data and non-real-time data operates by receiving non-real-time data and receiving real-time data. A windowing operating system is executed for controlling the operation of an application program which is responsive to the non-real-time data, for conditioning a display device to display respective images representing the non-real-time data. A real-time display process is executed concurrently with, but independently from, the windowing operating system, for conditioning the display device to display respective images representing the real-time data concurrently with the display of the non-real-time data.

21 Claims, 4 Drawing Sheets

Hardware system

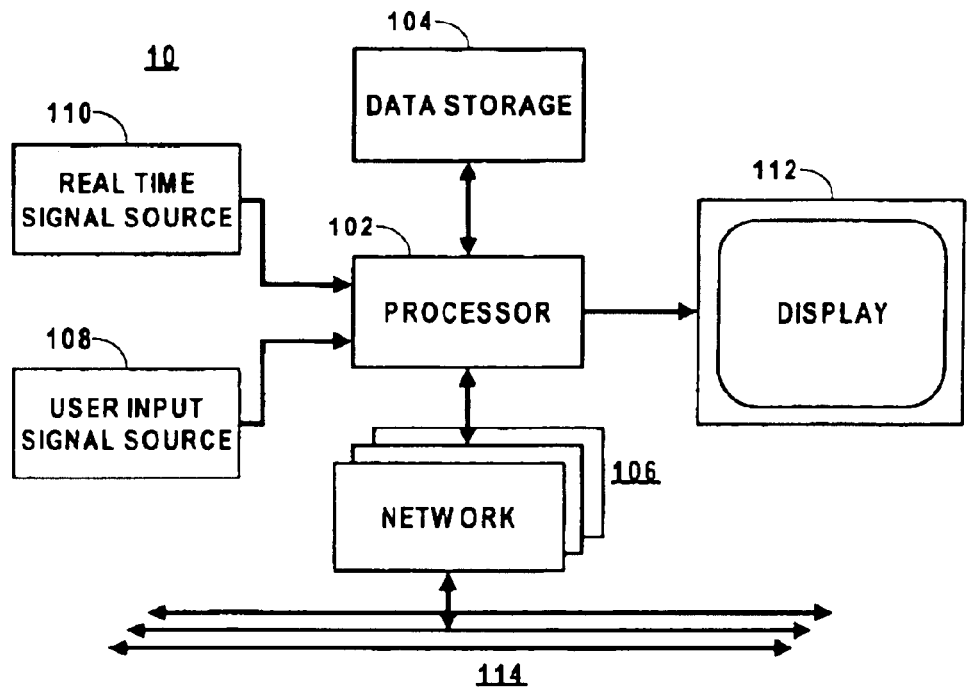
Fig. 1 – Hardware system
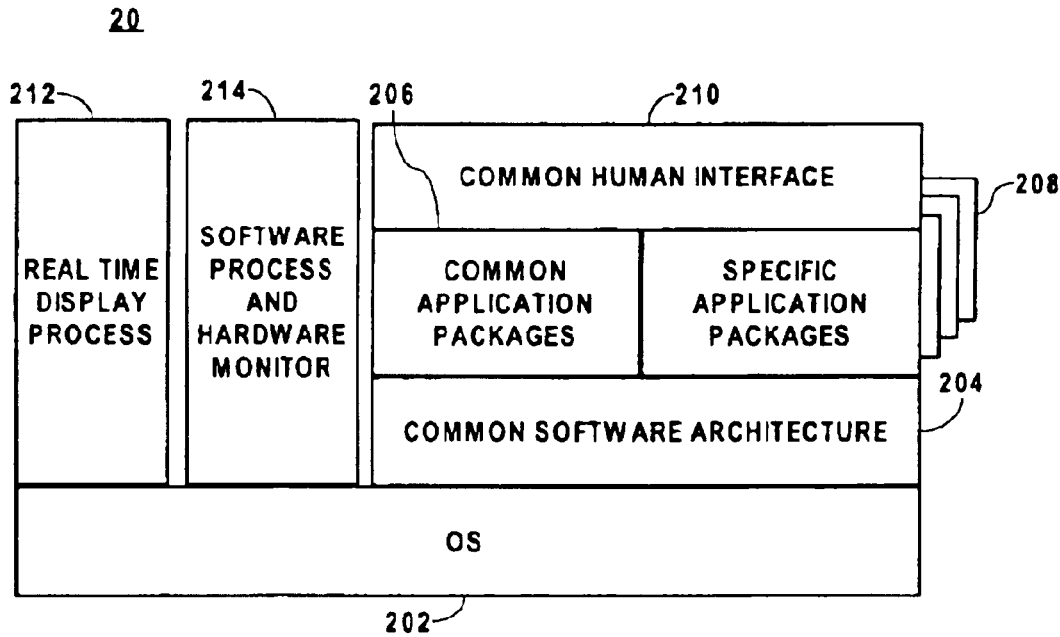
Fig. 2 – Software architecture

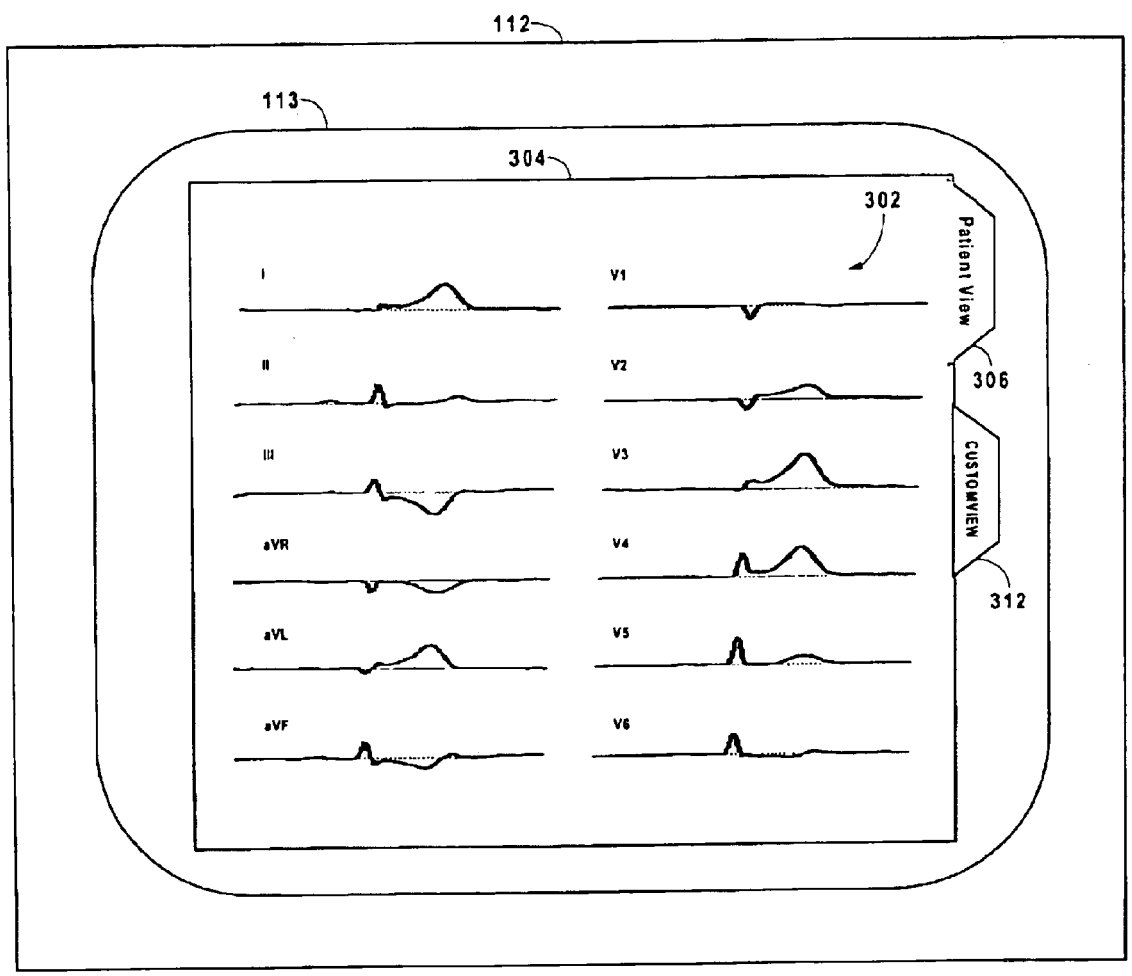
Fig. 3 – Patient view screen

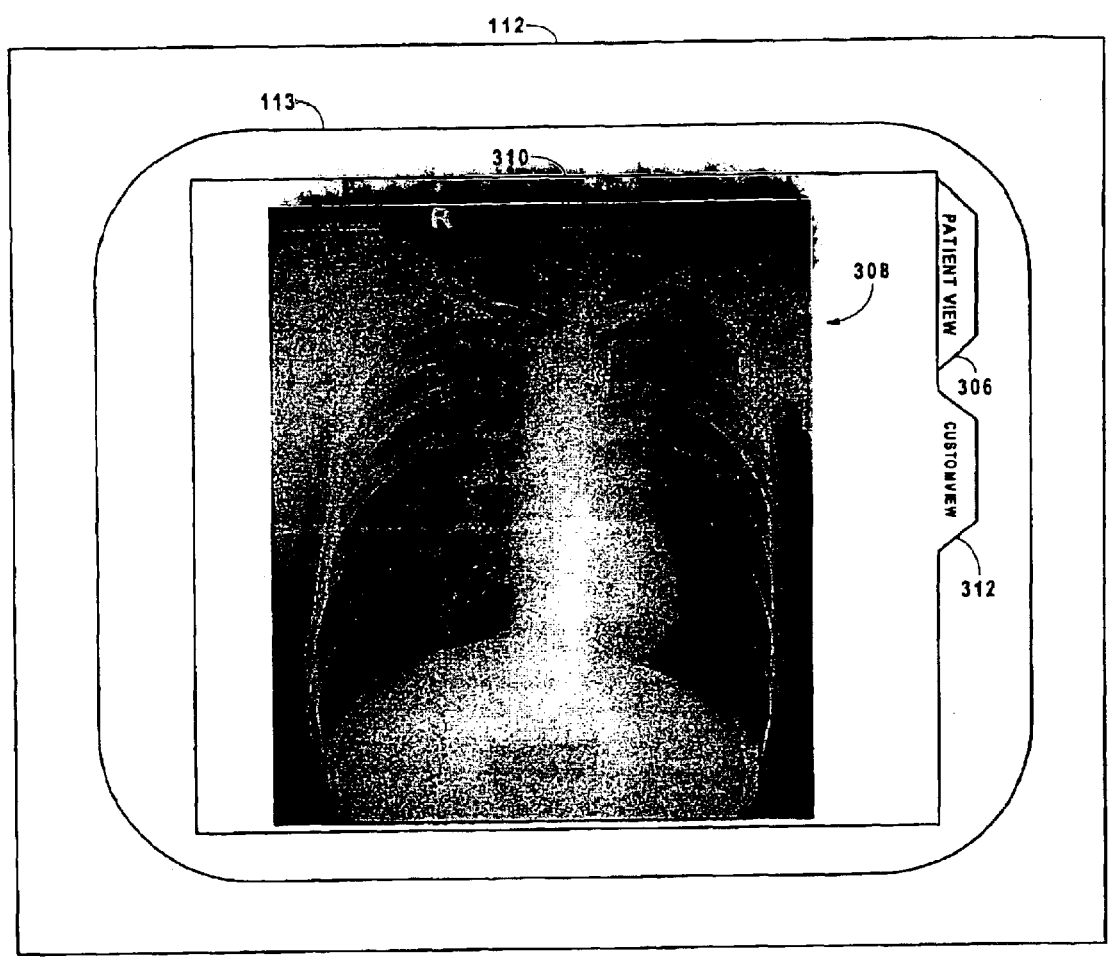
Fig. 4 – Custom view screen

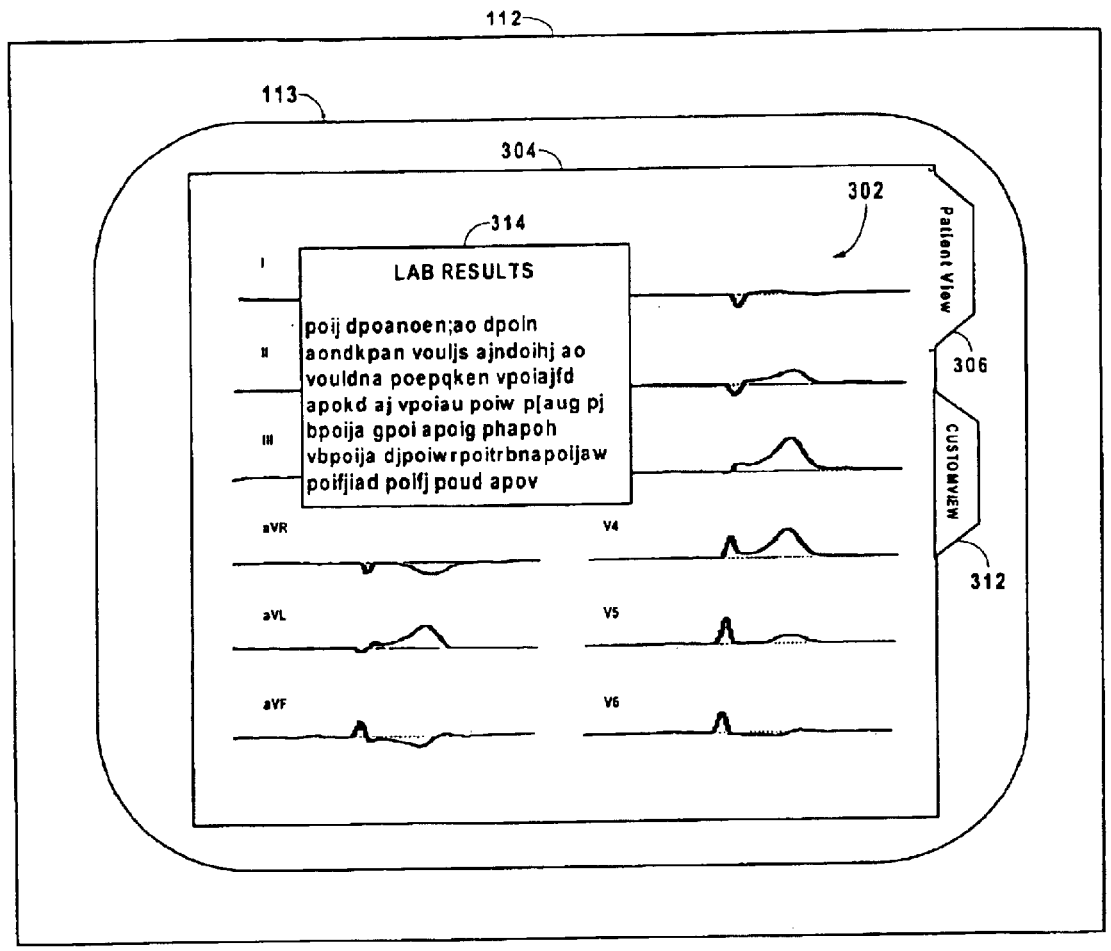
Fig. 5 – Pop-up screen

METHOD AND APPARATUS FOR CONCURRENTLY DISPLAYING RESPECTIVE IMAGES REPRESENTING REAL-TIME DATA AND NON REAL-TIME DATA

This is a non provisional application of provisional application serial No. 60/248,101, filed Nov. 13, 2000 by Ortlam et al.

FIELD OF THE INVENTION

The present invention relates to a display system for displaying images representing real-time data simultaneously with images representing non-real-time data.

BACKGROUND OF THE INVENTION

Systems for displaying images representing real-time data have a long history. For example, systems have long existed for displaying a waveform image representing real-time physiological data such as electrocardiogram (ECG) data. More recently, systems have been developed for simultaneously displaying multiple images representing respective real-time data. For example, current ECG systems can simultaneously display all 12 waveforms of a full 12 lead ECG. U.S. Pat. No. 6,104,948, issued Aug. 15, 2000 to Bogart et al., discloses a system for receiving a plurality of physiological real-time data from different sources, such as ECG, electroencephalogram (EEG), skin conductance information, oculometer derived look-point data, and skin temperature. The system also receives other real-time data such as cardiac cine-loop video. The system then simultaneously and synchronously displays a composite image containing the respective images representing all of the received real-time data. The composite image may be recorded utilizing a scan converter on a video tape recorder for future study.

Systems for simultaneously displaying images representing respective non-real-time data also exist. For example, computer windowing operating systems, such as UNIX X-windows, Apple Macintosh and Microsoft Windows permit programs to be written for displaying multiple images representing respective non-real-time data. For example, U.S. Pat. No. 5,956,013, issued Sep. 21, 1999 to Raj et al. discloses a Microsoft Windows based system for receiving prerecorded ECG data from, e.g. a Holter heart monitor, and displaying a first image of a waveform representing several seconds of ECG data, and simultaneously displaying a second image of a selected number (e.g. one to five) of heartbeat waveforms atop each other aligned on their R waves.

Further systems exist for simultaneously displaying images representing real-time data and images representing non-real-time data. For example, computer systems operating under the control of the above mentioned windowing operating systems have been designed to include a real-time data collection device, and images representing the gathered real-time data have been displayed simultaneously with images representing non-real-time data. U.S. Pat. No. 4,845,653, issued Jul. 4, 1989 to Conrad et al. discloses a system in which a plurality of two parameter data fields are simultaneously displayed representing respective views of the same multi-parameter data. This data may be displayed in real-time as it is received. A user may define an outline enclosing an area in one of the data fields, and the data points corresponding to those within that area are highlighted in the other data fields. Further non-real-time information, derived from the enclosed data points, may also be displayed.

One skilled in the art will understand that the computer windowing operating systems, described above, make it relatively simple to design and implement a program to simultaneously display real-time and non-real-time data. Consequently, many programs have been written to perform a wide variety of very desirable tasks for these operating systems. One skilled in the art will also understand that such operating systems are not reliable and will often require restarting, resetting or rebooting, particularly when executing a program or multiple programs including multiple tasks or threads. However, it is always desirable for systems to operate with high reliability. In some applications, such as medical monitoring equipment, it is imperative that the system operate with the highest possible reliability. For example, for an ECG monitor, the display of the waveform images representing the ECG data must never be interrupted, and further must proceed with a minimum latency time between receipt of the real-time ECG data and the display of that data.

One skilled in the art will understand that display of non-real-time data simultaneously with display of the real-time (e.g. ECG) data would be useful. For example, a doctor analyzing a patient's real-time ECG display might desire to simultaneously display textual lab results for the patient, or an image of an X-ray, or data from the patient's chart, or even information from a pharmaceutical company's web site. The skilled practitioner will also appreciate the advantages provided by using a windowing operating system as the basis for such a system, such as familiarity of use, ease of programming and the availability of a wide variety of programs. Finally, the skilled practitioner will appreciate that, while display of non-real-time information is important and desirable, a malfunction in the non-real-time data display program (such as must be expected when using such windowing operating systems) must not be allowed to interrupt the display of the real-time ECG data under any circumstances. Thus, a system which permits simultaneous display of real-time and non-real-time data using existing windowing operating systems, but which does not permit malfunction in the display of the non-real-time data to interrupt the display of the real-time data is desirable.

BRIEF SUMMARY OF THE INVENTION

In accordance with principles of the present invention, a method and apparatus for concurrently displaying respective images representing real-time data and non-real-time data operates by first receiving non-real-time data and receiving real-time data. A windowing operating system is executed for controlling the operation of an application program which is responsive to the non-real-time data, for conditioning a display device to display respective images representing the non-real-time data. A real-time display process is executed concurrently with, but independently from, the windowing operating system, for conditioning the display device to display respective images representing the real-time data concurrently with the display of the non-real-time data.

BRIEF DESCRIPTION OF THE DRAWING

In the drawing:

FIG. 1 is a block diagram of a computer system according to principles of the present invention; and FIG. 2 is a software architecture diagram illustrating an architecture according to principles of the present invention, executing on the processor for controlling the system;

FIG. 3, FIG. 4 and FIG. 5 are screen diagrams illustrating images displayed by the system according to the present invention.

DETAILED DESCRIPTION OF THE INVENTION

FIG. 1 is a block diagram of a computer system 10 according to principles of the present invention. In FIG. 1, a processor 102 has a first bidirectional terminal coupled to a data storage device 104 and one or more further bidirectional terminals coupled to corresponding network interface circuits (NIC) 106. Each NIC 106 is coupled to a corresponding network 114. The networks 114 may include a real-time network, such as a patient area network with a required latency time of less than 200 ms from patient sensor to display, a ward area network with latency on the order of seconds, and/or a hospital network which has no real-time latency requirement. One or more of the networks 114, most likely the hospital network, may also include a bridge (not shown) to a wide area network such as the internet. A source 108 of a user input signal is coupled to a first input terminal of the processor 102 and a source 110 of a real-time input signal is coupled to a second input terminal of the processor 102. An output terminal of the processor 102 is coupled to an input terminal of a display device 112.

In operation, the processor 102 receives program code and data from the data storage device 104. The processor 102 controls the operation of the system 10 under the direction of the received program code. The architecture of this program code will be described in detail below. In general, the processor 102 receives real-time data from the real-time data source 110 and/or the real-time network 114 and conditions the display device 112 to display images representing the real-time data. For example, the real-time signal source 110 and/or real-time network 114 could include an ECG module having electrodes intended to be connected to a patient. The signals from the electrodes are processed by the processor 102 which, in turn, conditions the display device 112 to display images representing a real-time 12 lead ECG. In accordance with medical monitoring system requirements, this real-time display has a maximum latency of 200 milliseconds from receipt of the data from the ECG module to display of that data on the display device 112 and must have the maximum practical reliability.

The processor 102 further monitors the user input signals from the user input signal source 108. The user input signals may be derived from, e.g. a keyboard and/or mouse (not shown) or any other input device. The processor 102 then controls the system 10 in response to the user input signals. These user input signals can control aspects such as size and location of the display of the real-time images, e.g. 12 lead ECG images, and/or selection and display of non-real-time data. For example, in response to identification information received from the user via the user input signal source 108, a non-real-time application program is executed so that non-real-time data may be retrieved from specified files in the data storage device 104, or from specified locations on the network 114, e.g. patient chart data, lab results or X-ray images from the hospital LAN server or other data from the internet, via the NIC 106. The controller 102 conditions the display device 112 to display images representing the retrieved non-real-time data and/or other data received from the user input signal source 108 on the display device 112 simultaneously with the images representing the real-time data from the real-time data source 110 and/or real-time network 114. The processor 102 also controls the operation of the system 10 as a whole in response to user input signals from the user input signal source 108 in a manner to be described in more detail below.

In a preferred embodiment, the processor 102 operates under the control of a windowing operating system, and in the illustrated embodiment, the windowing operating system is the Microsoft NT operating system. FIG. 2 is a diagram illustrating the architecture of the program code executed by the processor 102 to control the system 10. An operating system (OS) 202 provides services for the rest of the software system 20 consisting of functions and data common to all other software modules which execute on the system 20. For example, the message transmission system necessary for multiprocessing, and the graphics display interface, is administered in the OS 202. In addition, processes and threads may be initiated and terminated, and memory may be allocated to and deallocated from a process and/or thread, in the OS 202.

Parameters related to the operation of the software system 20 are also maintained in the OS 202. For example, data related to total processor usage; the length of the message queue for each process and thread; available memory; virtual memory page access faults; working set size and paging rate; a count of handles allocated to processes and threads; the proportion of processor time being used by each process or thread; the rate of data transmission on the network 114; and responsiveness of respective processes and threads to user input signals, among other things, may all be determined by and stored in the OS 202. It is also possible for physical parameters of the hardware system 10 to be received by circuitry under control of the OS 202 and data related to these parameters to be stored in the OS 202. For example, data such as central processing unit (CPU) chip temperature, power supply voltage, hard disk usage elapsed time, and hard disk storage free space, may be maintained in the OS 202.

In general, the program 20 is a three tiered architecture. The first tier is a common software architecture 204 which provides a software interface between application packages (206 and 208) and the OS 202. The common software architecture 204 provides the application program interfaces (APIs) for the application programs. By providing APIs, the operating system simplifies the task of programming applications. Functions, such as requesting initiation of a thread or allocation of memory, are provided to the application programmers through simple function calls, all in a known manner.

Common and specific application packages, 206 and 208, form a second tier. Common application packages 206 refer to applications which are provided by the providers of the operating system. These are generally applications which are used by most or all of the users of the operating system. The common application packages 208 can include text editors, image viewers, HTML viewers (web browsers), etc. Furthermore, portions of these common application packages may be used by the specific application packages 208. Specific application packages 208 are those providing special functions required by the system. In general, a single specific package 208 provides a desired special processing. The common and specific application packages, 206 and 208 receive operating system services via APIs in the common software architecture 204, and generate images to be displayed on the display device 112 through a common human interface 210. The human interface 210 forms a third tier. The human interface 210 is provided as a part of the operating system and provides another API for allowing common and specific application programs 206 and 208 to produce images on the display device 112, all in a known manner.

The portion of the software architecture 20 described so far is the standard architecture for non-real-time programs implemented on the Windows NT operating system. This portion of the software architecture executes as a single executable, calling for functions through the various APIs described above, spawning tasks and threads, and requesting and returning memory as required.

In the illustrated embodiment, an additional process 212 receives the real-time ECG signals from the real-time signal source 110 and/or real-time LAN 114, and processes the received real-time ECG signals to generate images for the display device 112 representing a 12 lead ECG corresponding to the received signals in a manner to be described in more detail later. The real-time display process 212 receives operating system services from the OS 202 only. It does not use services in the common software architecture 204 or the common human interface 210. This process executes as a second executable, independent of, but coordinated with the non-real-time executable described above. In addition, the real-time process 212 is implemented as a single thread which processes data from receipt from the data source to generation of the display image, insuring minimum latency.

The following operational parameters all relate to the Windows NT environment. Other windowing operating systems have similar parameters. In the illustrated embodiment, all non-real-time applications, and all processes and threads spawned by those applications, are assigned a priority of 13 or less, the real-time process 212 is assigned a higher priority (>13) than any of the processes or threads in the non-real-time process, giving the real-time application higher execution priority. Therefore, the real-time display process 212 processes messages from the OS 202 in a rate determinate manner. One skilled in the art will understand that this guarantees that all messages sent to the real-time display process 212 will be processed properly because the real-time process has a higher priority and will not be interrupted by non-real-time threads.

In addition, the 'application boost' parameter for the non-real-time processes and threads is set to "None". The real-time network 114 must use LAN switches instead of hubs. Routers are not allowed in the network 114. The computing environment is further controlled to minimize the invocation of Interrupt Service Routines and Deferred Procedure Calls. The working set (page frames used to contain memory pages in a virtual memory environment) for the real-time process 212 is locked down using a device driver in the OS 202 so that the working set is not swapped out to the storage device 104 during virtual memory swaps. Finally, a GDI probe in the OS 202 locks down an instance of the GDI engine and its associated resources for use exclusively by the real-time process 212.

The architecture 20 illustrated in FIG. 2, thus, includes two executables, one for handling the non-real-time data and one for handling the real-time data. This architecture provides the following advantages. First, the separation of executables provides robustness. There are two separate message queues maintained by the OS 202. If one queue becomes blocked, the other will still operate. Second the display device 112 is driven with two separate and independent graphical display interfaces. The common human interface 210 provides only a single window display interface in which different windows are arranged in a parent-child relation, requiring message and/or event propagation from child to parent and back again. By providing a separate graphical interface for the real-time display process, there is no parent-child relationship with other windows, improving reliability and decreasing message and/or event propagation. This, in turn, decreases the latency time from receipt of real-time data from the real-time signal source 110 to display of images representing that data on the display device 112.

One skilled in the art will understand that, to improve readability and controllability by the user, it is desirable to make the graphical 'look' of the real-time display process 212 the same as, or very similar to, the 'look' of the non-real-time display generated under the control of the common human interface 210. In the illustrated embodiment, the graphical interface generated by the real-time display process 212 is designed to graphically integrate with the graphical interface generated by the common human interface 210. More specifically, in the illustrated embodiment the graphical interface of both the real-time display process 212 and the common human interface 210 use a tabcard paradigm. The process for generating the combined display will be described in more detail below. One skilled in the art will understand that the particulars of the 'look' are not germane to the present invention, only that they are the same or similar for the non-real-time and real-time processing.

The image generated by the real-time process 212 is combined with the image generated by the non-real-time process 204, 206, 208, 210 by use of the graphics device interface (GDI) engine built into the OS 202. One skilled in the art will understand that the GDI engine receives image descriptive instructions from applications. In response to these instructions, the GDI updates the values stored in the video memory in the hardware video adapter (not shown) to represent the combined images of the application programs. The video adapter, in turn, generates video signals for the display device 112 in response to the contents of the video memory.

The real-time process 212 requests and receives an identifying graphics handle from the OS 202 in the usual manner.

The single-thread real-time process 212 then receives the real-time signals from the real-time signal source 110 and, identified by the assigned graphics handle, generates instructions for the GDI engine for displaying the desired real-time image. The real-time process 212 then makes a call to the instance of the GDI assigned exclusively to the real-time process 212 to provide these instructions. This GDI engine is assigned the same high priority as the real-time process 212 so that its execution may not be interrupted by the non-real-time applications. The GDI engine, in turn, conditions the display device 112 to display the combined real-time and non-real-time images via the display device driver.

More specifically, in the illustrated embodiment where the real-time signals are ECG signals, the real-time display process thread receives the ECG electrode signals from the real-time signal source 110 or the real-time LAN 114 and generates a bit map representing the instantaneous waveform images of the 12 ECG lead signals. The real-time process thread 212 then directly calls the GDI in the OS 202 and gives it instructions (bit block transfer instruction) to transfer the bit map to the video memory in the display device 112. The GDI engine transfers the bit map to the appropriate location in the video memory in the video adapter.

Using this technique, the real-time image may be integrated with the non-real-time images using the same 'look', as provided by the GDI of the OS 202. One skilled in the art will understand that is may also be possible to interface directly with the display device adapter, although this presents many security and reliability problems. One skilled in the art will further understand that other interface methods, such as DirectX may also be used to provide the image representative signals to the video adapter.

FIG. 3 is a screen diagram illustrating real-time images displayed by the system according to the present invention under the control of the real-time display process 212. FIG. 3 illustrates an exemplary 12 lead ECG image. In FIG. 3, the display device 112 includes a display screen 113, such as the face of a CRT, which displays respective images 302 of 12 real-time waveforms (I, II, III, aVR, aVL, aVF, V1, V2, V3, V4, V5 and V6). These waveforms are updated in real-time within the latency limit (200 ms) described above. The waveforms are displayed as if they were contained in a tabbed page 304 having an associated tab 306 which includes indicia ("Patient View") identifying the contents of that associated page. An additional tab 312 will be described in detail below.

FIG. 4 illustrates a display screen 113 in which a non-real-time display image 308 of a chest X ray is displayed in a tabbed page 310. The tabbed page 310 includes an associated tab 312 which includes indicia ("Custom View") identifying the contents of the associated page. This tabbed page 310 overlays the real-time data tabbed page associated with the tab 306, completely obscuring it. One skilled in the art will understand that the image illustrated in FIG. 4 represents only a single tabbed page, but that more than one such tabbed page may be simultaneously made available, each representing different non-real-time data. Furthermore, each tabbed page may simultaneously display more than one window, each displaying an image representing respective non-real-time data. For example, as described above, textual lab results or web pages may be simultaneously displayed on different tabbed pages or in overlapping windows on a single tabbed page, in a manner controlled by the Windows NT operating system.

As described above, and as is well known to one skilled in the art, it is possible for the non-real-time processing software to malfunction. Should this happen, it is possible for the real-time (ECG) information to be blocked from sight by the image of the non-real-time information displayed on the display device 212. For example, should the non-real-time portion (204, 206, 208, 210) of the program architecture 20 malfunction while displaying the image illustrated in FIG. 4, the images representing the real-time ECG data 302 will be hidden. To provide a solution to this problem, the OS 202 is conditioned to be responsive to data from the user input signal source 108 to activate the tabbed page 304 displaying images 302 representing the real-time information from the real-time signal source 110, as in FIG. 3. For example, a specific key or key combination, e.g. <Control-R>, on a keyboard is specially recognized by the OS 202, and when recognized, the real-time display 302, being generated by the real-time display process 212, is displayed, atop the frozen non-real-time image 308. The key or key combination is termed a 'hot key', and the functions necessary to implement this are part of the Windows NT operating system.

In another situation, the images representing the real-time information may be partially obscured by an image representing non-real-time information. FIG. 5 is a screen diagram illustrating the real-time images 302 atop which a window 314 including textual lab results is displayed. The window 314, generated by the non-real-time portion (204, 206, 208, 210) of the software architecture 20, partially obscures the real-time images 302. That portion of the real-time images 302 which remains visible continues to display the real-time data received from the real-time signal source 110. However, the real-time portion behind the window 314 is not visible. Should the non-real-time portion (204, 206, 208, 210) of the program architecture 20 malfunction while displaying the image illustrated in FIG. 5, the portion of the images representing the real-time ECG data 302 obscured by the window 314 will be hidden. In this case, the OS 202 recognizes signals from the user input signal source 108 representing a mouse click in the area of the display screen 113 outside of the window 314 and activates the real-time images 302, making them completely visible. Alternatively, the hot key combination, described above, may also be used to activate the real-time images 302, making them visible.

The inventor has also realized that it is possible to monitor the operation of the non-real-time portion (204, 206, 208, 210) of the software (20) to identify indications that the non-real-time portion has malfunctioned or is in danger of malfunctioning. In response to such indications, it is possible to control the non-real-time portion in such a manner that the malfunction is automatically corrected or avoided.

One skilled in the art will understand that the non-real-time processes should not be allowed to interfere with the operation of the real-time process. As described above, the OS 202 maintains information concerning the operation of the application programs, the operating system and the computer system in general. However, during standard operations, the operating system does not monitor this information or perform any functions based on the values of this information.

The architecture 20 illustrated in FIG. 2 further includes a software and hardware monitor 214. The monitor 214 monitors the information (described above) which is maintained in the OS 202. The monitor 214 then performs actions based on the values of the information in the OS 202. The monitor process 214 is made very simple to ensure maximum reliability and is assigned the highest or a very high priority to ensure that it is always able to execute.

In general, the OS 202 maintains an indication of the usage of various resources. The monitor process 214 retrieves the usage values from the OS 202 and monitors the amount of resources available. If the amount decreases to a dangerously low level, corrective actions are taken. For example, in an appropriate case, non-real-time processes are terminated to free resources taken by those processes for use by the real-time process. That is, if one of the non-real-time processes malfunctions, then that process is terminated. The terminated process may then be automatically restarted. Alternatively, notifications may be sent as an alert to a user that a problem exists. In response to such an alert, the user can take corrective actions.

More specifically, there are several groups of resources monitored by the process monitor 214: the availability of general resources; the availability of system resources; the availability of computer resources; and the operation of the non-real-time processes, tasks and threads. The following four tables describe respective resource groups monitored by the monitor process 214. Within each table, a first column sets out the resource monitored. The second column sets out an explanation of the check, e.g. why it is important, what effect it might have, and how it is monitored, etc. The third column sets out the parameters which indicate a failure for that resource. Unless indicated otherwise, these parameters are variable and any threshold value may be changed by the user at any time. One skilled in the art will further understand that even those parameters indicated by a specific number are only related to the illustrated embodiment and a range of permissible numbers is available for those parameters. The fourth column sets out the actions which are taken when a failure is indicated. Table 1 illustrates memory resource checks. Table 2 illustrates system resource checks. Table 3 illustrates computer resource checks. Table 4 illustrates process checks.

TABLE 1

Memory Resource checks

| Specific Check | Check Explanation | Failure Parameters | Failure Action |
|---|---|---|---|
| Page Fault count. | If the Page Fault count is growing, then the system's memory is too heavily loaded, | The Page Fault count above a predetermined threshold | An attempt will be made to increase Working Set size of the real-time process and to decrease the Working Set sizes of all non-real-time processes. |
| | | The real-time process's Page Fault count is still above the threshold. | All non-real-time applications will be terminated in turn, until Page Fault count returns to normal or there are no more non-real-time applications. |

TABLE 2

System Resource Checks

| Specific Check | Check Explanation | Failure Parameters | Failure Action |
|---|---|---|---|
| Total Processor Usage | Too high usage will lead to overall system unresponsiveness. If using a multiprocessor computer, System: Total Processor Time for the system as a whole, and Processor: Processor Time for each processor may be monitored separately. | Over 80% | All non-real-time applications will be terminated in turn. |
| Processor Queue Length | Sustained presence of two or more tasks in the queue indicates processor congestion | Sustained count of 2 or greater lasts longer than 5 minutes | All non-real-time applications will be terminated in turn. |
| Available Memory | The Available Memory counter indicates how many bytes of memory are currently available for use by processes. Low values for the Available Bytes counter can indicate that there is an overall shortage of memory on the computer or that an application is not releasing memory. | Available memory is below a predetermined amount. | An attempt will be made to force all non-real-time processes to be paged out. If that does not help, all non-real-time applications will be terminated in turn. |
| Paging Rate | The Pages/sec counter indicates the number of pages that either were retrieved from disk due to hard page faults or written to disk to free space in the working set due to page faults. A high rate for the Pages/sec counter could indicate excessive paging. Monitor the Memory: Page Faults/sec counter to make sure that the disk activity is not caused by paging. | Hard disk paging rate is too high. | An attempt will be made to force all non-real-time processes to be paged out. If that does not help, all non-real-time applications will be terminated in turn. |

TABLE 3

Computer Resource Monitor Checks

| Specific Check | Check Explanation | Failure Parameters | Failure Action |
|---|---|---|---|
| Network status. | Ping time shows the rate of data exchange on the network. If a ping times out, it means that the connection is broken or unacceptably slow. | Ping time is longer than a predetermined interval. | A high-priority notification is sent to the system-wide Notification component. |
| CPU chip temperature. | CPU Chip temperature rising too high indicates malfunctioning in the CPU cooling system and may lead to processor damage and malfunction of the processes. | The temperature is above a predetermined threshold. | A medium-priority notification is sent to the system-wide Notification component. |
| Input voltage from the power source. | Voltage outside of the standard range will lead to the partial or complete system shutdown. Wild power fluctuation may be indicative of power source's failure. | Voltage is outside of predetermined limits. | A medium-priority notification is sent to the system-wide Notification component. |
| Hard disk spinning time. | Hard disk has a usage time limit documented by the manufacturer. When the disk spinning time approaches the specified limit, hard disk service or replacement may be needed to prevent failures. | Disk spinning time exceeds a specified interval. | A single low-priority notification is sent to the system-wide Notification component. |
| An important logical hard disk's partition is low on space | Either the windowing operating system partition, or real-time system partition (if it is not installed on the operating system partition) of hard disk is nearing its capacity. Some data has to be removed from the partition. | The partition is over 80% full. | A high-priority notification is sent to the system-wide Notification component. |

TABLE 4

Process Checks

| Specific Check | Check Explanation | Failure Parameters | Failure Action |
|---|---|---|---|
| Handle count | If the Handle count for a process is increasing, the process is probably leaking handles. | Handle count reaches a threshold level and keeps steadily increasing after that. | The process will be terminated. |
| Working Set size | If the Working Set size of a process is increasing, the process is probably leaking memory or allocating excessive amounts of memory. | The Working Set size reaches a threshold level | An attempt will be made to empty the Working Set. If the Working Set could not be emptied or is still above the threshold, the process will be terminated. |
| Verify responsiveness of processes with GUI | Responsiveness means that the process has retrieved messages from its message queue recently. If it has not, it is probably hung up. | The process has not retrieved messages from its message queue within last 10 seconds. | The process will be terminated. |
| CPU load | If a process consistently spends large percentage of process's time executing processor instructions, it is probably running a busy loop. | The process consistently consumes over 90% of process's time to execute processor instructions. | The process will be terminated. |

A system operating in the manner described above will be able to display images representing real-time data with a high degree of reliability and minimum latency simultaneously with images representing non-real-time data.

What is claimed is:

1. A system for concurrently displaying respective images representing real-time data and non-real-time data, comprising:

a source of signals representing real-time data;
a source of signals representing non-real-time data;
a display device for displaying images;
a processor, coupled to the real-time data source, the non-real-time data source and the display device, the processor:
   executing a windowing operating system controlling the operation of an application program for receiving non-real-time data and conditioning the display device to display an image representing the non-real-time data; and
   executing a real-time display process, for receiving the real-time data and conditioning the display device to display an image representing the real-time data concurrently with the display of the non-real-lime data; the execution of the real-time display process being independent of the execution of the operating system.

2. A system for concurrently displaying respective images representing real-time data and non-real-time data, comprising:

a source of signals representing real-time data;
a source of signals representing non-real-time data;
a display device for displaying images;
a processor, coupled to the real-time data source, the non-real-time data source and the display device, the processor:
   executing a windowing operating system controlling the operation of an application program for receiving non-real-time data and conditioning the display device to display an image representing the non-real-time data; and
   executing a real-time display process, for receiving the real-time data and conditioning the display device to display an image representing the real-time data concurrently with the display of the non-real-time data; the execution of the real-time display process being independent of the execution of the operating system, wherein the real-time data signal source is a network with a specified latency limit; and the real-time display process receives the real-time data and displays the real-time data representative image within the specified latency limit.

3. A system for concurrently displaying respective images representing real-time data and non-real-time data, comprising:

a source of signals representing real-time data;
a source of signals representing non-real-time data;
a display device for displaying images;
a processor, coupled to the real-time data source, the non-real-time data source and the display device, the processor:
  executing a windowing operating system controlling the operation of an application program for receiving non-real-time data and conditioning the display device to display an image representing the non-real-time data; and
  executing a real-time display process, for receiving the real-time data and conditioning the display device to display an image representing the real-time data concurrently with the display of the non-real-time data; the execution of the real-time display process being independent of the execution of the operating system wherein the real-time display process operates as a single thread.

4. The system of claim 3 wherein the real-time display process thread is assigned a priority higher than the application program.

5. The system of claim 3 wherein:
the windowing operating system provides a graphics display interface for conditioning the display device to display a specified image; and
the real-time display process thread provides instructions to the graphics display interface to display the real-time image.

6. A system for concurrently displaying respective images representing real-time data and non-real-time data, comprising:

a source of signals representing real-time data;
a source of signals representing non-real-time data;
a display device for displaying images;
a processor, coupled to the real-time data source, the non-real-time data source and the display device, the processor:
  executing a windowing operating system controlling the operation of an application program for receiving non-real-time data and conditioning the display device to display an image representing the non-real-time data; and
  executing a real-time display process, for receiving the real-time data and conditioning the display device to display an image representing the real-time data concurrently with the display of the non-real-time data; the execution of the real-time display process being independent of the execution of the operating system, wherein the application program may malfunction such that the non-real-time data representative image obscures the real-time data representative image;
the system further comprises a source of user input signals; and
the processor, in response to a user input signal, reveals the real-time data representative image.

7. The system of claim 6, wherein the user input signal source comprises a keyboard, and the user input signal comprises a key combination.

8. The system of claim 6, wherein the user input signal source comprises a mouse, and the user input signal comprises a mouse click.

9. A system for concurrently displaying respective images representing real-time data and non-real-time data, comprising:

a source of signals representing real-time data;
a source of signals representing non-real-time data;
a display device for displaying images;
a processor, coupled to the real-time data source, the non-real-time data source and the display device, the processor:
  executing a windowing operating system controlling the operation of an application program for receiving non-real-time data and conditioning the display device to display an image representing the non-real-time data; and
  executing a real-time display process, for receiving the real-time data and conditioning the display device to display an image representing the real-time data concurrently with the display of the non-real-time data; the execution of the real-time display process being independent of the execution of the operating system, wherein the windowing operating system maintains information relating to the availability of resources; and
the processor further executes a monitor process for monitoring the resource information and for taking corrective action if the resource information indicate that the availability of a resource is below a predetermined level.

10. The system of claim 9 wherein the resource information maintained by the windowing operating system maintains comprises information related to:
memory resources;
system resources;
computer resources; and
process resources.

11. The system of claim 9 wherein the corrective action taken by the processor comprises:
modifying execution parameters of the application program;
terminating the application program; and
sending a notification to the user.

12. A method for concurrently displaying respective images representing real-time data and non-real-time data, comprising the steps of:
receiving non-real-time data;
receiving real-time data;
executing a windowing operating system for controlling the operation of an application program responsive to the non-real-time data, for conditioning a display device to display respective images representing the non-real-time data;
executing a real-time display process, independently of the windowing operating system, for conditioning the display device to display respective images representing the real-time data concurrently with the display of the non-real-time data.

13. A method for concurrently displaying respective images representing real-time data and non-real-time data, comprising the steps of:

receiving non-real-time data;

receiving real-time data;

executing a windowing operating system for controlling the operation of an application program responsive to the non-real-time data, for conditioning a display device to display respective images representing the non-real-time data;

executing a real-time display process, independently of the windowing operating system, for conditioning the display device to display respective images representing the real-time data concurrently with the display of the non-real-time data and further comprising the step of executing the real-time display process as a single thread.

14. The method of claim 13 further comprising the step of assigning the real-time display process thread a higher priority than the application program.

15. The method of claim 13 wherein the windowing operating system execution step comprises the step of executing a graphics display interface to receive instructions for generating images; and the real-time display process execution step comprises the step of providing instructions to the graphics display interface to display the respective images representing the real-time data.

16. A method for concurrently displaying respective images representing real-time data and non-real-time data, comprising the steps of:

receiving non-real-time data;

receiving real-time data;

executing a windowing operating system for controlling the operation of an application program responsive to the non-real-time data, for conditioning a display device to display respective images representing the non-real-time data;

executing a real-time display process, independently of the windowing operating system, for conditioning the display device to display respective images representing the real-time data concurrently with the display of the non-real-time data and further comprising the steps of, if the application program malfunctions such that the non-real-time data representative image obscure the real-time data representative image:

receiving user input data; and revealing the real-time representative data in response to the user input data.

17. The method of claim 16 wherein the step of receiving user input data comprises the step of receiving a key combination from a keyboard.

18. The method of claim 16 wherein the step of receiving user input data comprises the step of receiving a mouse click from a mouse.

19. A method for concurrently displaying respective images representing real-time data and non-real-time data, receiving non-real-time data;

receiving real-time data;

executing a windowing operating system for controlling the operation of an application program responsive to the non-real-time data, for conditioning a display device to display respective images representing the non-real-time data;

executing a real-time display process, independently of the windowing operating system, for conditioning the display device to display respective images representing the real-time data concurrently with the display of the non-real-time data wherein:

the step of executing the windowing operating system comprises the step of maintaining information relating to the availability of resources; and the method further comprises the step of:

executing a monitor process for monitoring the resource information; and taking corrective action if the resource information indicates that the availability of a resource is below a predetermined level.

20. The method of claim 19 wherein the step of monitoring the resource information comprises the steps of:

monitoring memory resources;

monitoring system resources;

monitoring computer resources; and monitoring process resources.

21. The method of claim 19 wherein the step of taking correcting action comprises the steps of:

modifying execution parameters of the application program;

terminating the application program; and sending a notification to the user.

* * * * *